US010098699B1

(12) United States Patent
Buck

(10) Patent No.: US 10,098,699 B1
(45) Date of Patent: Oct. 16, 2018

(54) SYSTEM AND METHOD FOR APPLYING STERILE MEDICAL GLOVES

(71) Applicant: James Buck, Benbrook, TX (US)

(72) Inventor: James Buck, Benbrook, TX (US)

( * ) Notice: Subject to any disclaimer, the term of this patent is extended or adjusted under 35 U.S.C. 154(b) by 0 days.

(21) Appl. No.: 14/942,955

(22) Filed: Nov. 16, 2015

(51) Int. Cl.
*A47G 25/90* (2006.01)
*A47F 1/04* (2006.01)
*A61B 19/04* (2006.01)
*A41D 19/00* (2006.01)
*A61B 19/00* (2006.01)

(52) U.S. Cl.
CPC ........ *A61B 19/045* (2013.01); *A41D 19/0055* (2013.01); *A47F 1/04* (2013.01); *A47G 25/90* (2013.01); *A61B 19/44* (2013.01); *A47G 25/904* (2013.01); *A61B 2019/046* (2013.01); *A61B 2019/442* (2013.01); *A61B 2019/448* (2013.01)

(58) Field of Classification Search
CPC . A61B 19/045; A61B 19/44; A61B 2019/046; A61B 2019/442; A61B 2019/448; B65D 83/0835; B65D 83/0841; B65D 83/0445; B65D 83/0472; A47F 1/04; G07F 11/04; A47G 25/90; A47G 25/904; A41D 19/0055
See application file for complete search history.

(56) References Cited

U.S. PATENT DOCUMENTS

| | | | | | |
|---|---|---|---|---|---|
| 3,067,001 | A | * | 12/1962 | McCollum | A61B 42/00 128/898 |
| 4,889,266 | A | * | 12/1989 | Wight | A61B 42/40 206/278 |
| 4,909,413 | A | * | 3/1990 | McCutcheon | A47G 25/904 221/1 |
| 8,807,402 | B2 | * | 8/2014 | Backhaus | A41D 19/0072 223/111 |
| 2002/0113079 | A1 | * | 8/2002 | Corbett | A47G 25/904 221/303 |
| 2010/0263695 | A1 | * | 10/2010 | Hampe | B08B 3/041 134/113 |
| 2011/0108587 | A1 | * | 5/2011 | Williams | A47G 25/904 223/111 |
| 2012/0204517 | A1 | * | 8/2012 | Stollery | B65B 35/58 53/447 |
| 2013/0199581 | A1 | * | 8/2013 | Christopherson | B08B 5/026 134/103.2 |

* cited by examiner

*Primary Examiner* — Ismael Izaguirre
(74) *Attorney, Agent, or Firm* — Damon R. Hickman

(57) ABSTRACT

A method of preventing contamination of gloves for the medical industry by using negative pressure to inflate the glove the allowing a user to merely insert their hands without touching the exterior portion of the gloves. The apparatus is comprised of a strip of sealed gloves, a regularly sterilized vacuum chamber, a vacuum pump, and a controller.

16 Claims, 6 Drawing Sheets

SYSTEM AND METHOD FOR APPLYING STERILE MEDICAL GLOVES

BACKGROUND

1. Field of the Invention

The present invention relates generally to applying sterile gloves, and more specifically to a system and method for inflating a sterile medical glove thereby allowing a user to insert their hand without contamination of the exterior of the glove.

2. Description of Related Art

The healthcare industry spends enormous amounts of money and effort into maintaining a sterile environment around patients. Sterile gloves are one way the industry prevents the spread of drug resistant bacteria. Conventionally medical gloves are stored in a box. When a user is ready to glove up, i.e. apply their gloves, they reach into the box and grab a glove. The mere act of reaching into the box of gloves can contaminate the grabbed glove and the rest of the gloves in the container. Even the act of applying two pairs of gloves does not prevent the possible contamination. Contamination occurs from the bacteria on the user's hand being transferred onto the gloves when the user's hand is inserted into the box of gloves. While there are many systems and methods for applying medical gloves well known in the art, considerable room for improvement remains.

DESCRIPTION OF THE DRAWINGS

The novel features believed characteristic of the embodiments of the present application are set forth in the appended claims. However, the embodiments themselves, as well as a preferred mode of use, and further objectives and advantages thereof, will best be understood by reference to the following detailed description when read in conjunction with the accompanying drawings, wherein:

Figure 1:
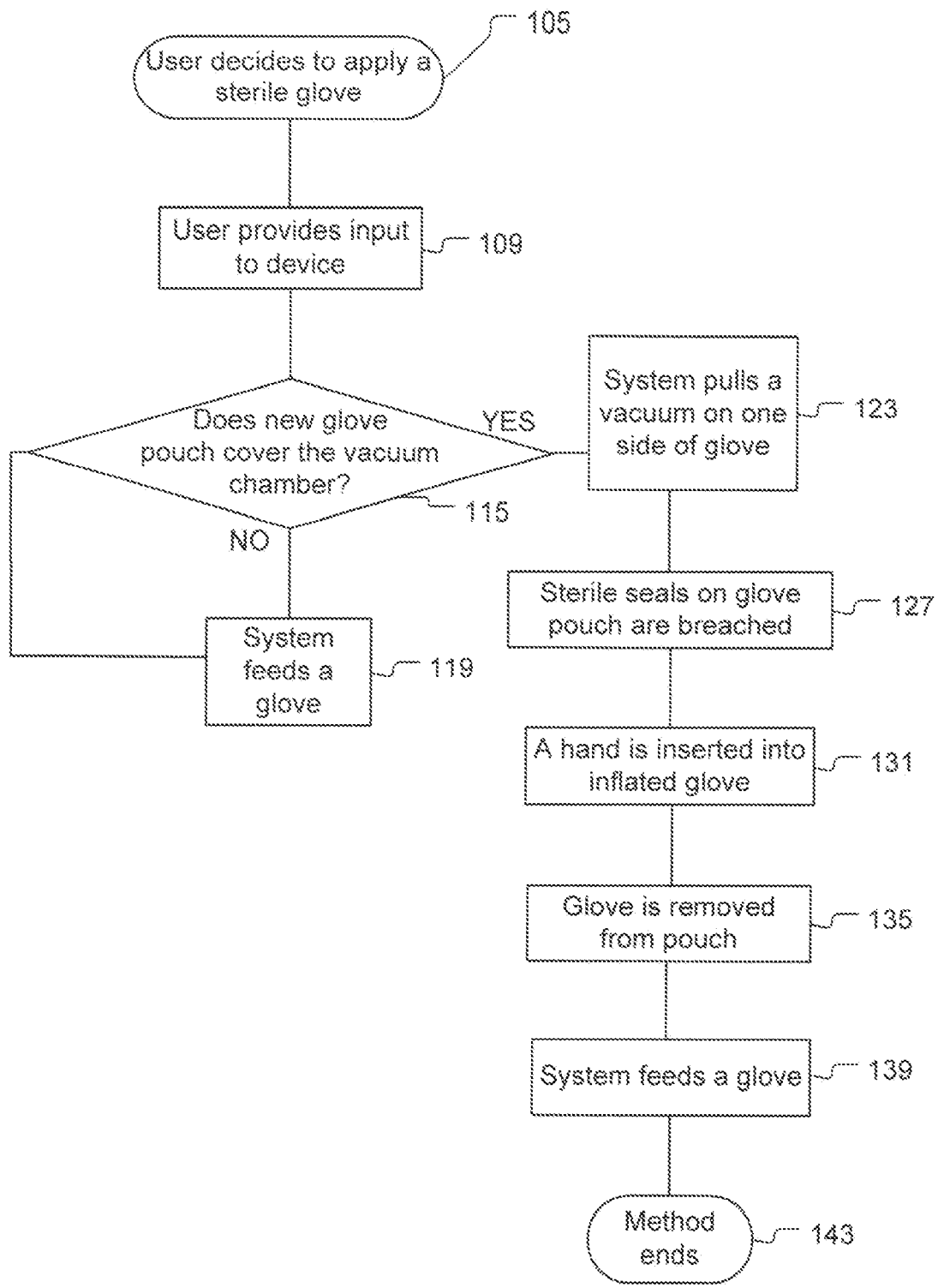
FIG. 1 is a flow chart of a method for applying sterile medical gloves illustrated according to the present application.

While the assembly of the present application is susceptible to various modifications and alternative forms, specific embodiments thereof have been shown by way of example in the drawings and are herein described in detail. It should be understood, however, that the description herein of specific embodiments is not intended to limit the invention to the particular embodiment disclosed, but on the contrary, the intention is to cover all modifications, equivalents, and alternatives falling within the spirit and scope of the present application as defined by the appended claims.

DETAILED DESCRIPTION OF THE PREFERRED EMBODIMENT

Illustrative embodiments of a system and method for applying sterile medical gloves are provided below. It will of course be appreciated that in the development of any actual embodiment, numerous implementation-specific decisions will be made to achieve the developer's specific goals, such as compliance with assembly-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

Referring now to FIG. 1 in the drawings, a flow chart of a method for applying sterile medical gloves illustrated according to the present application. Method 101 is comprised of steps to prevent the glove from being contaminated during insertion of the user's hand into the glove. A user must make a decision to wear a glove 105. After the user decides to glove up the user provides an input 109 to the gloving machine. The input to the gloving machine preferably is in the form of depressing a floor switch with the user's foot. Other methods of inputting the user's intentions to the machine are contemplated such as a light curtain sensing an impended hand or the machine detecting the radio-frequency identification from the user's badge as they are adjacent the machine. The method requires a new glove pouch be in place for the method to work. Therefore, a determination is made if a new, sealed, and unused glove pouch is in the proper location 115. For example, does the new glove pouch cover the vacuum chamber, if not then the system feeds a new glove pouch 119 into position.

Once the new, sealed, and unused glove pouch is in place a vacuum is pulled on an exterior portion of the glove 123. The glove has an interior portion and an exterior portion. The interior portion of the glove is the portion of the glove that will be in direct contact with the user's hand when the glove is worn. The exterior portion of the gloves is the portion of the gloves that will not be in direct contact with the user's hands. The seals on the glove pouch are breached 127. Preferably the user breaches the seals by pushing their hands into the openings thereby breaking the seals open. Once the seals are opened the effect of pulling a vacuum on the exterior portion of the glove causes the glove to inflate due to the pressure difference between the interior portion of the glove and the exterior portion of the glove. A hand is inserted into the inflated glove 131. At this point the user has a gloved hand and removes their hand from the machine with the glove on their hand 135. The act of removing the user's hand dislodges the glove from the pouch. Alternatively the system shears the end of the glove from the pouch by a die cutter or other shearing implement. Once the user's hand has been removed then another glove pouch is fed 139 or cycled into place. The method ends 143 or repeats if another glove is needed by the user. Additionally the system sterilizes the vacuum chamber as needed to maintain a sterile vacuuming area by use of an ultraviolet light.

Figure 2:
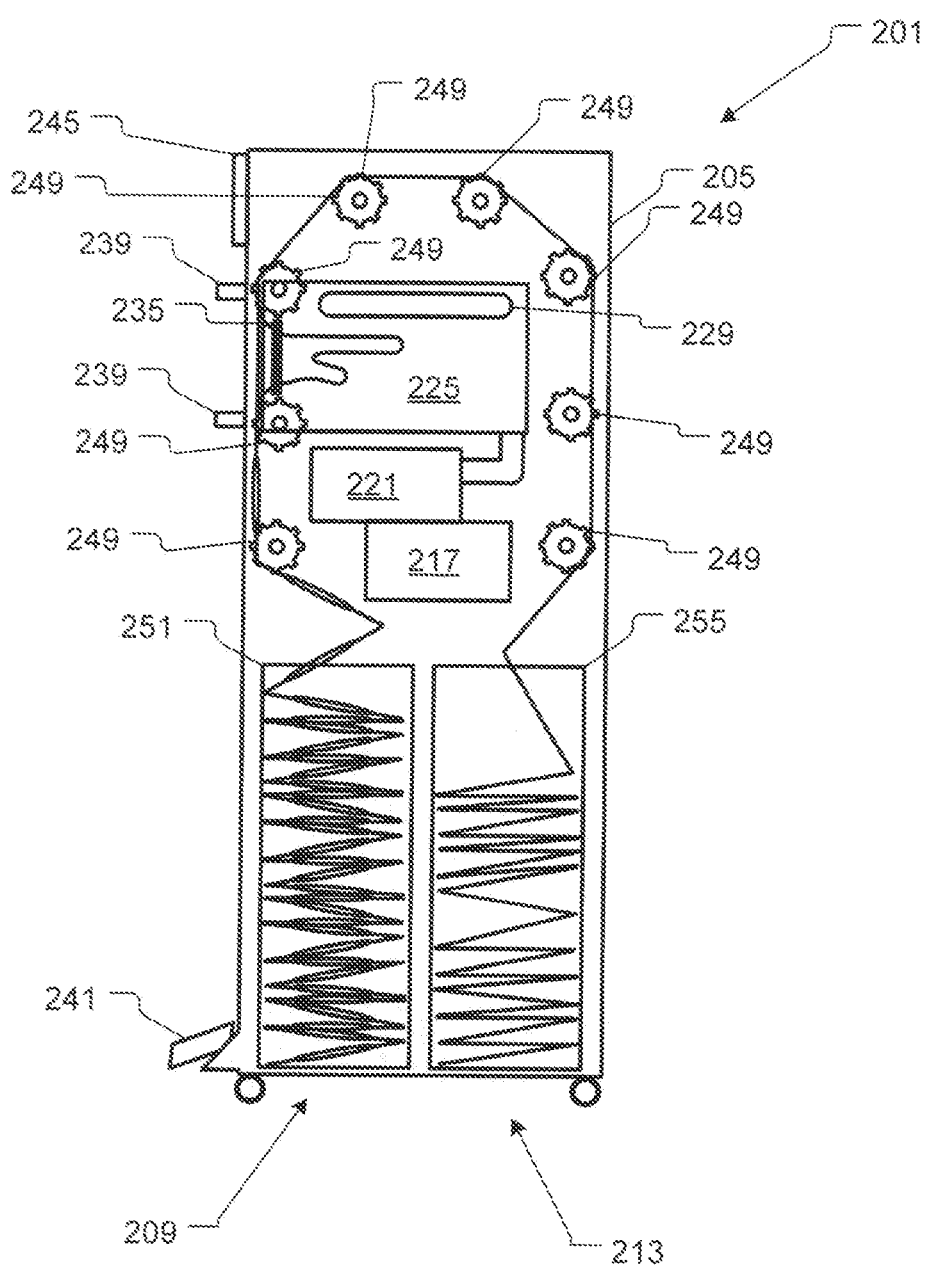
FIG. 2 is a side view of an apparatus for applying sterile medical gloves illustrated according to the present application.
Figure 3:
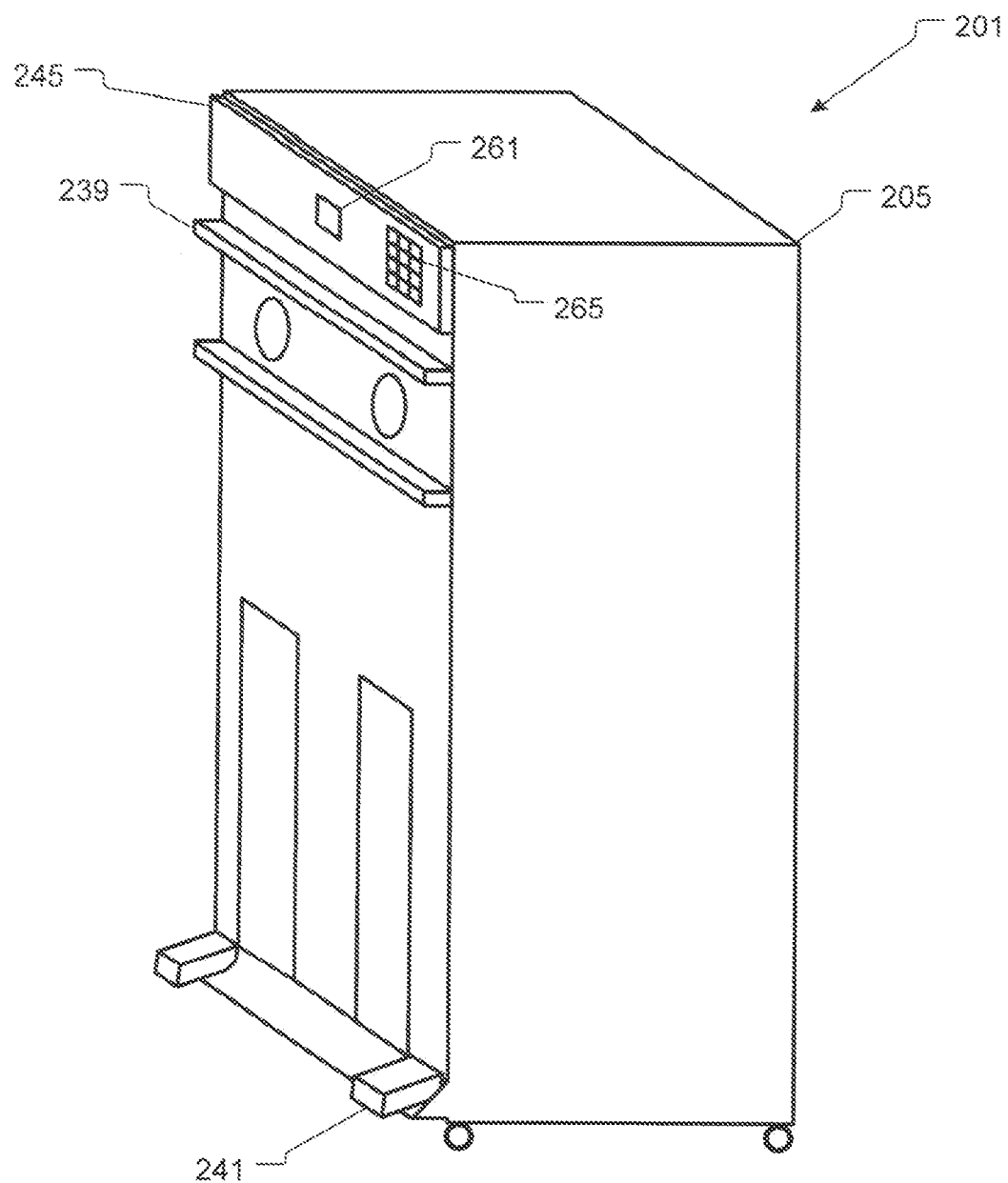
FIG. 3 is a perspective view of an apparatus for applying sterile medical gloves illustrated according to the present application.

Referring now also to FIG. 2 in the drawings, a side view of an apparatus for applying sterile medical gloves illustrated according to the present application. Referring now also to FIG. 3 in the drawings, a perspective view of an apparatus for applying sterile medical gloves illustrated according to the present application. System 201 is comprised of an enclosure 205 with wheels, a plurality of sealed glove pouches 209, a plurality of used glove pouches 213, a controller 217, a vacuum pump 221, a vacuum chamber 225 pneumatically coupled to the vacuum pump 221 by hoses and filters and valves, a sterilizer 229, a cutter 235, a light curtain sensor 239, a foot switch 241, a control panel 245, and a track system 249. Track system 249 is comprised of motors, gears, sprockets, pins, belts, pulleys, and/or chains to allow the system to move the continuous strip of sealed pouches.

The enclosure 205 provides a location for the various elements of the system 201 to be stored and used safely. The plurality of sealed gloves pouches 209 are stored until use in first container 251 that is removable. The plurality of used gloves pouches 213 are stored after use in a second container 255 that is removable. The plurality of sealed glove pouches 209 and the plurality of used glove pouches 213 are connected together to form a single chain of pouches. As the gloves are applied the chain of pouches is moved and utilized. Typically, the system starts with a chain of new glove pouches and as the gloves are applied the chain becomes a chain of used glove pouches as they move from the first container 251 across the vacuum chamber 225 and into the second container 255.

Controller 217 operates the track system 249 to position the plurality of new glove pouches to a location where a glove can be applied. Controller 217 uses sensors to advance the glove pouch to the location where a glove can be applied. The sensors can be the foot switch 241, the light curtain 239, or the RFID reader 261. The operator is able to enter in a billing code either from the key pad 265, the RFID reader 261, or by a bar code reader. Additionally the controller 217 can read RFID tags or chips and barcodes on the glove pouches to determine the amount of pouches remaining and or amount of pouches used. Controller 217 is able to connect to a network and provide feedback to a hospital about glove usage and the location of the enclosure.

The sterilizer 229, preferably an ultra violet light source or an infrared light, operates at regular intervals to maintain a sterile environment inside the vacuum chamber 225. Cutter 235 is preferable a die cutter than moves a short distance to shear the end of the glove from the pouch so the user can remove their hand from the machine with the glove on their hand. The system as shown in FIG. 3 can be used by two hands concurrently. This speeds up the process of gloving up before service is rendered in a hospital. Alternatively each opening in the machine could be associated with a differently sized glove. For example, one opening could be associated with a large glove and another opening is associated with a small glove.

Figure 4:
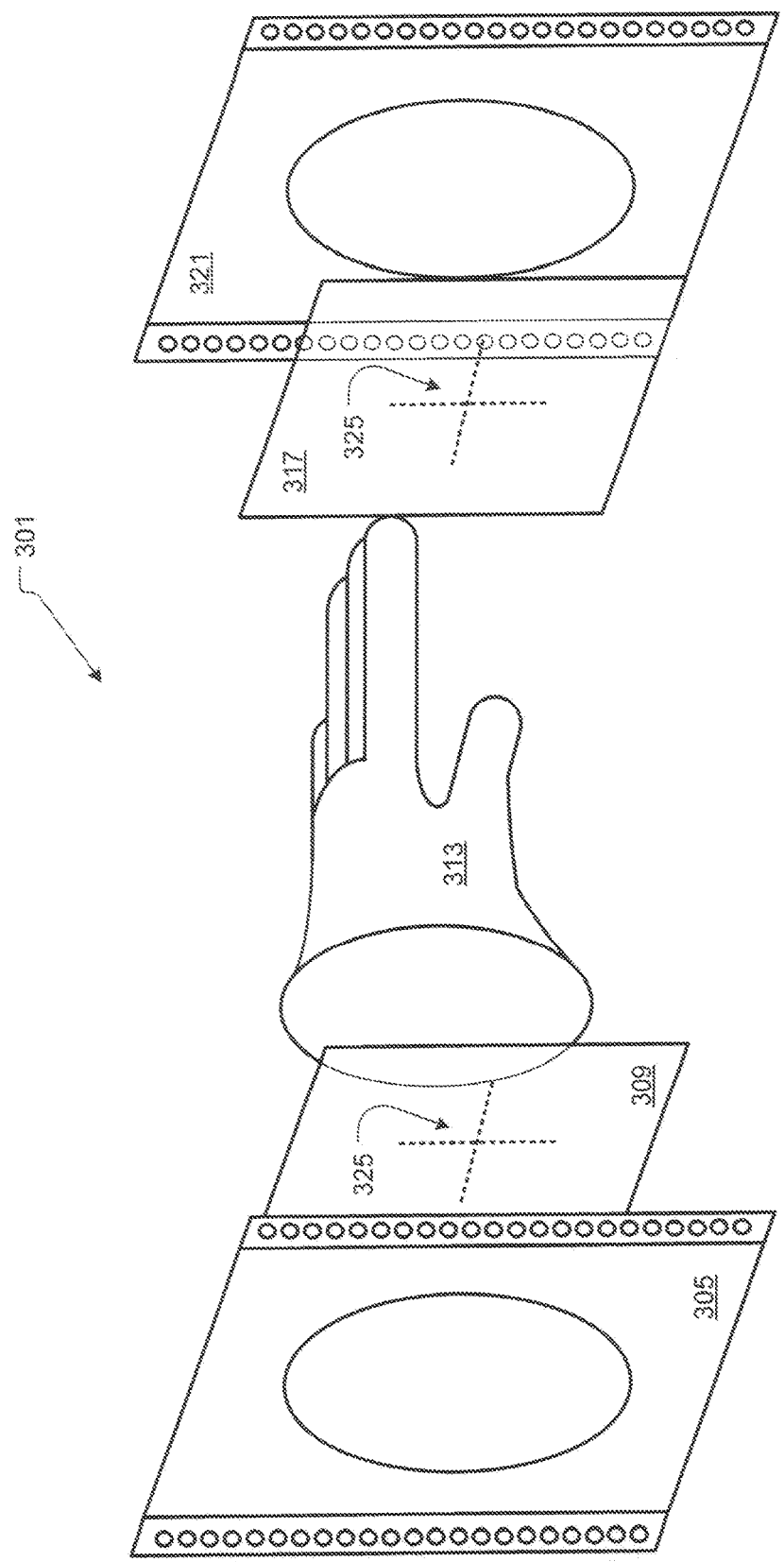
FIG. 4 is an exploded view of a feedable sterile medical glove container illustrated according to the present application.

Referring now also to FIG. 4 in the drawings, an exploded view of a feedable sterile medical glove container illustrated according to the present application. Glove pouch 301 is comprised of a first layer 305 or holder, a first seal 309, a glove 313, a second seal 317, and a second layer 321 or holder. All the layers are combined to form a sealed sterile pouch that can be moved along a path in the machine. Pouch 301 is preferably vacuum sealed to reduce contamination and to reduce the footprint of the pouch. Both the first layer 305 and the second layer 321 are preferably fabricated from paper or plastic and are configured to be fed. Both the first layer 305 and the second layer 321 are punched longitudinally along both edges with regularly spaced engagement holes that engage with sprocket wheels or toothed belts which move the pouch through the system. When fed through the system the strip is simply a continuous piece. Both the first layer 305 and the second layer 321 have a sets of aligned holes along a first and a second edge. The holes align when the first layer 305 and the second layer 321 retain the seals and the glove. Both the first layer 305 and the second layer 321 have openings configured that the glove 313 is visible and centered in the pouch. Both the first seal 309 and the second seal 317 are preferably plastic and are weakened, preferably scored 325, in the center adjacent the glove such that a user's hand can break the seal open. First seal 309 and second seal 317 are preferable heat sealed together around the glove. The cuff of the glove is retained by being sandwiched between the first layer 305 and the second layer 321. The retainment is sufficient that the force of inflating the glove doesn't dislodge the glove but weak enough that the user can push the glove out of the pouch once the glove is applied. Alternatively a die cutter is used to sever the glove 313 from the pouch 301. Glove 313 alternatively further comprises a plurality of circular ridges or rims that form the edges of the glove after the glove is removed from the pouch or holder Pouch 301 is configured with a first surface and a second surface. First surface or exterior side faces the user. Second surface or interior side faces the vacuum chamber. The opening of glove 313 faces the first surface and the user. The fingers of the glove 313 face the second surface and the vacuum chamber. This configuration allows a user to insert their hand from outside the machine into the glove located inside the machine.

Figure 5:
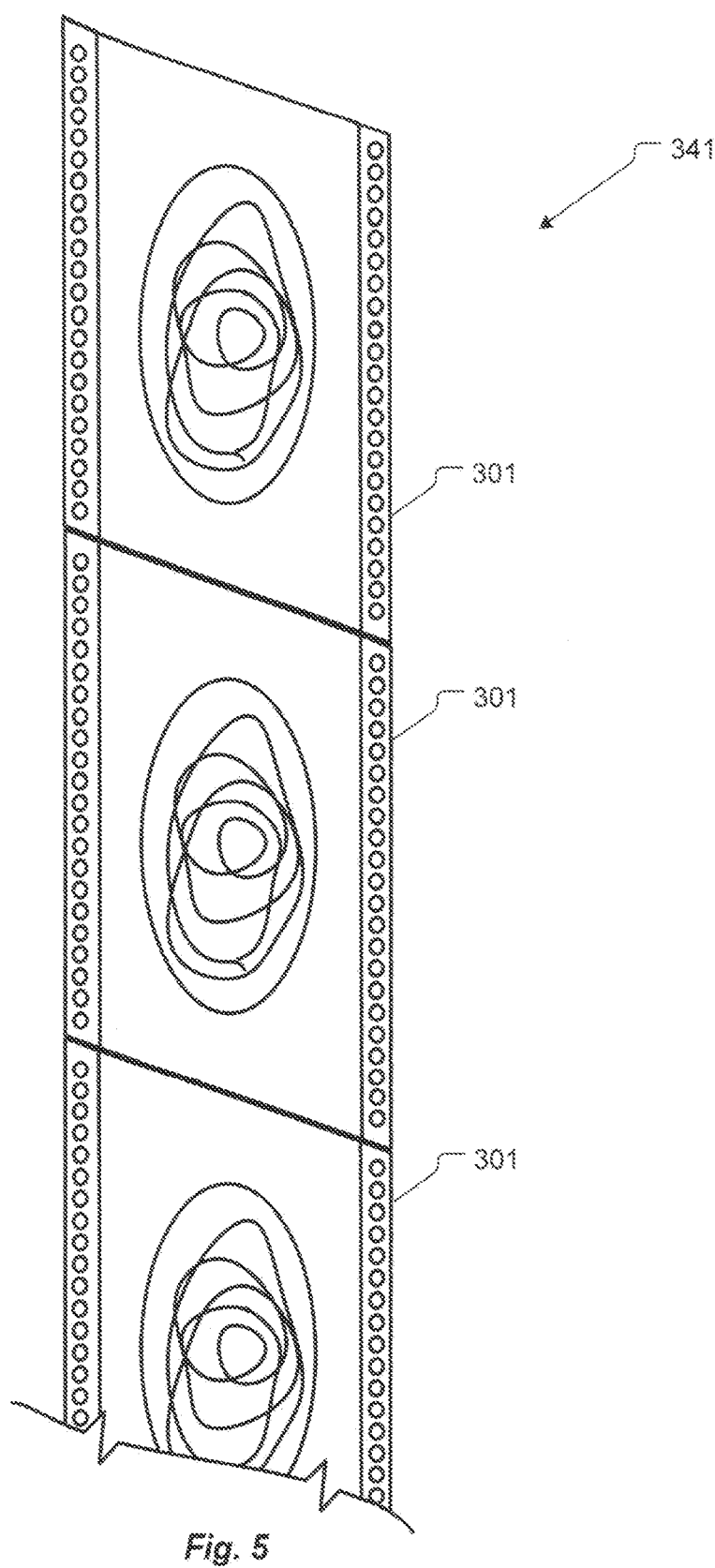
FIG. 5 is a perspective view of a strip of feedable sterile medical glove containers illustrated according to the present application.

Referring now also to FIG. 5 in the drawings, a perspective view of a strip of feedable sterile medical glove containers illustrated according to the present application. Strip 341 is comprised of several individual pouches 301 to form a feedable device capable of being moved by gears, spokes, and or cogs. The continuous form strip 341 is designed for use with appropriate strip-feed mechanisms. Other names for continuous strip include fan-fold strips, sprocket feed strips, tractor-feed strips, and pin feed strips.

Figure 6:
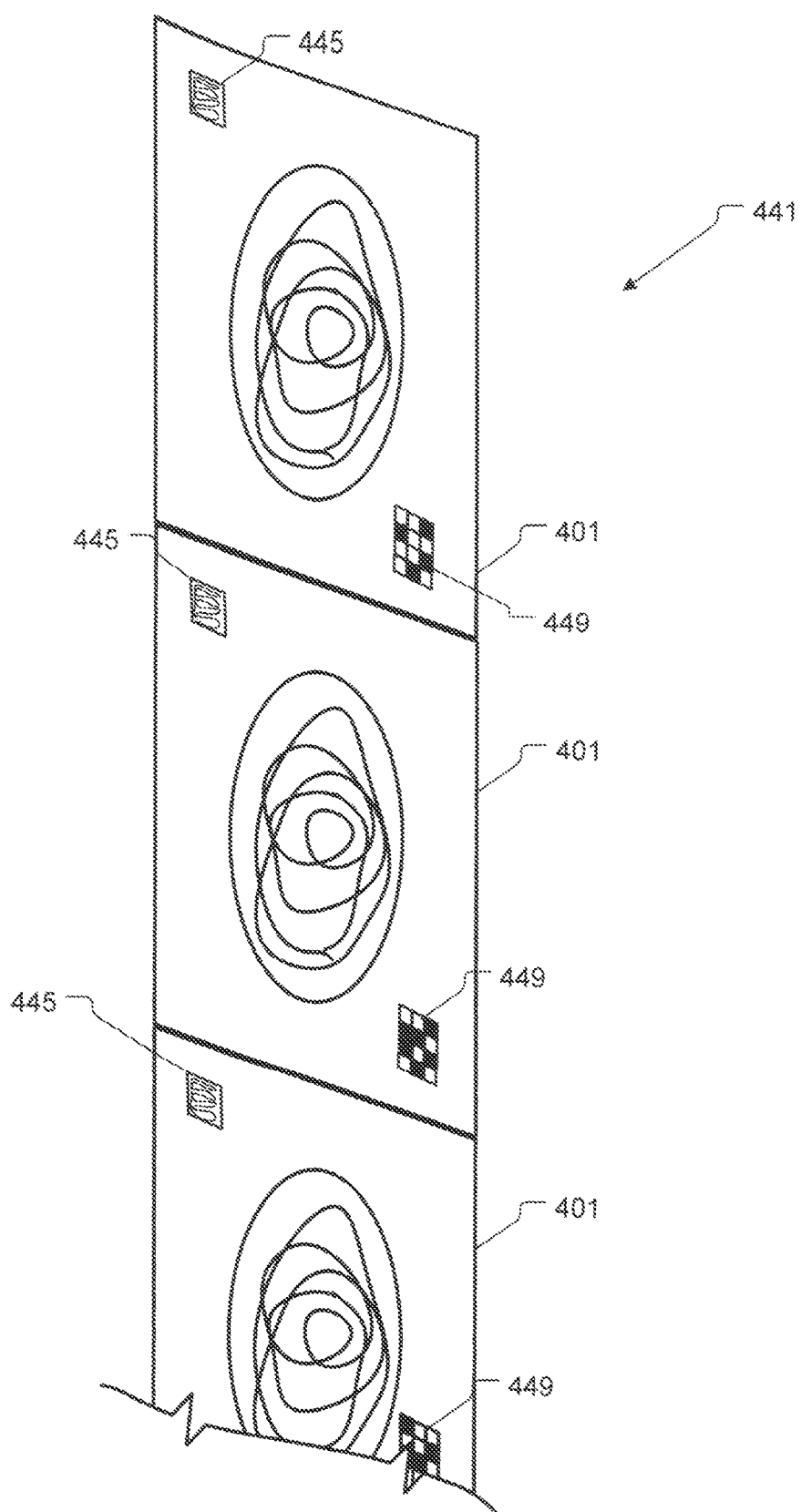
FIG. 6 is a perspective view of an alternative strip of feedable sterile medical glove containers illustrated according to the present application.

Referring now also to FIG. 6 in the drawings, a perspective view of an alternative strip of feedable sterile medical glove containers illustrated according to the present application. Strip 441 is comprised of several individual pouches 401 to form a feedable device capable of being moved by wheels. Strip 441 does not use tracks like strip 341 as the edges of strip 441 does not include a plurality of holes. Each of the pouches 401 in the strip 441 further comprises an RFID tag 445 and a barcode 449. The RFID tags 445 and the barcodes 449 allow the system to count the number of gloves used and the number of gloves remaining. This information can be linked to the hospital network to track usage of gloves for reordering purposes. Furthermore, when combined with an employee identification, such as the RFID tag on the employee's badge read from scanner 261, the hospital can track usage of gloves on a per employee basis.

While the preferred use of strip 441 is inside a machine being moved along a path for the automated application of sterile gloves onto a user's hand it should be apparent that strip 441 or pouch 301 does not require the user of a machine. Pouch 301 or strip 441 or the equivalent are capable of being used by hand. A user grabs the edge of the pouch 301 and inserts their own hand into the glove. Even though the glove isn't inflated the user can break the seals with their hand and push through to break the glove free from the holder. Furthermore, a nurse can hold a pouch with two hands for a another doctor or nurse to apply a sterile glove to a hand.

It is apparent that an assembly and method with significant advantages has been described and illustrated. The particular embodiments disclosed above are illustrative only, as the embodiments may be modified and practiced in different but equivalent manners apparent to those skilled in the art having the benefit of the teachings herein. It is therefore evident that the particular embodiments disclosed above may be altered or modified, and all such variations are considered within the scope and spirit of the application. Accordingly, the protection sought herein is as set forth in the description. Although the present embodiments are shown above, they are not limited to just these embodiments, but are amenable to various changes and modifications without departing from the spirit thereof.

What is claimed is:

1. A system for applying sterile medical glove, comprising:
   a vacuum pump;
   a vacuum chamber;
   a track system;
   a die cutter located in the vacuum chamber;
   a controller; and
   at least one glove;
   wherein the die cutter shears the at least one glove.

2. The system for applying sterile medical gloves according to claim 1, wherein the at least one glove is contained inside a pouch.

3. The system for applying sterile medical gloves according to claim 1, further comprising:
   a foot switch.

4. The system for applying sterile medical gloves according to claim 1, further comprising:
   a light curtain configured for activating the vacuum pump.

5. The system for applying sterile medical gloves according to claim 1, further comprising:
   a RFID sensor.

6. The system for applying sterile medical gloves according to claim 1, further comprising:
   a ultraviolet light located in the vacuum chamber.

7. The system for applying sterile medical gloves according to claim 2, further comprising:
   a plurality of pouches;
   wherein each pouch in the plurality of pouches comprises a glove; and
   wherein the plurality of pouches are formed into a continuous strip of pouches.

8. The system for applying sterile medical gloves according to claim 7, wherein each pouch in the plurality of pouches is configured for tracking along the track system.

9. A system for applying sterile medical gloves, comprising:
   a first pouch, having;
      a first holder;
      a second holder;
      a first seal;
      a second seal; and
      a glove located between the first seal and the second seal.

10. The system for applying sterile medical gloves according to claim 9, the first holder comprising:
    an opening centered around the glove;
    wherein the first holder is punched longitudinally along a first edge and a second edge with regularly spaced engagement holes.

11. The system for applying sterile medical gloves according to claim 9, wherein the first seal and the second seals are weakened adjacent the glove.

12. The system for applying sterile medical gloves according to claim 9, further comprising:
    a barcode located on the first pouch.

13. The system for applying sterile medical gloves according to claim 9, further comprising:
    an radio-frequency identification chip located on the first pouch.

14. The system for applying sterile medical gloves according to claim 9, further comprising:
    a vacuum pump;
    a vacuum chamber pneumatically connected to the vacuum pump;
    a track system configured for moving the first pouch;
    a controller;
    a ultraviolet light located in the vacuum chamber.

15. The system for applying sterile medical gloves according to claim 14, further comprising:
    a die cutter located in the vacuum chamber.

16. A method of applying sterile medical gloves, comprising:
    providing at least one glove in a sterile container;
    opening the sterile container;
    reducing the pressure exterior to the at least one glove relative to the pressure interior to the at least one glove;
    inserting a hand inside the glove;
    removing the glove from the container;
    wherein removing the glove from the container is accomplished by cutting the glove while the hand is inside the glove.

* * * * *